United States Patent
Zhang et al.

(10) Patent No.: US 7,441,894 B2
(45) Date of Patent: Oct. 28, 2008

(54) PSEUDO-ACCOMMODATIVE IOL HAVING DIFFRACTIVE ZONES WITH VARYING AREAS

(75) Inventors: Xiaoxiao Zhang, Fort Worth, TX (US); Steve VanNoy, Fort Worth, TX (US); Xin Hong, Arlington, TX (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 11/350,497

(22) Filed: Feb. 9, 2006

(65) Prior Publication Data

US 2007/0182921 A1    Aug. 9, 2007

(51) Int. Cl.
*G02C 7/06* (2006.01)
*A61F 2/16* (2006.01)

(52) U.S. Cl. .................. 351/168; 351/161; 623/6.27; 623/6.3; 623/6.31

(58) Field of Classification Search ............ 351/161, 351/164, 168; 623/6.24, 6.27, 6.3, 6.31
See application file for complete search history.

(56) References Cited

U.S. PATENT DOCUMENTS

| 5,344,447 A * | 9/1994 | Swanson ............... 623/6.3 |
| 5,699,142 A | 12/1997 | Lee et al. |
| 6,554,859 B1 * | 4/2003 | Lang et al. ............ 623/6.28 |
| 2003/0043342 A1 * | 3/2003 | Seidner ................. 351/161 |

FOREIGN PATENT DOCUMENTS

| EP | 0343067 A1 | 11/1989 |
| EP | 0367878 A1 | 5/1990 |
| WO | WO 9411765 A1 | 5/1994 |

* cited by examiner

*Primary Examiner*—Darryl J Collins
(74) *Attorney, Agent, or Firm*—Armando Pastrana, Jr.

(57) ABSTRACT

In one aspect of the invention, a trifocal ophthalmic lens is disclosed that includes an optic having at least one optical surface, and a plurality of diffractive zones that are disposed on a portion of that surface about an optical axis of the optic. At least two of those diffractive zones have different areas so as to cause broadening of optical energy profiles at a near and a far foci of the diffractive zones for generating an intermediate focus.

4 Claims, 7 Drawing Sheets

PSEUDO-ACCOMMODATIVE IOL HAVING DIFFRACTIVE ZONES WITH VARYING AREAS

BACKGROUND

The present invention relates generally to multifocal ophthalmic lenses, and more particularly, to trifocal ophthalmic lenses, such as trifocal intraocular lenses (IOLs).

A plurality of ophthalmic lenses are available for correcting visual disorders, such as cataract, myopia, hyperopia or astigmatism. For example, an intraocular lens (IOL) can be implanted in a patient's eye during cataract surgery to compensate for the lost optical power of the removed natural lens. Though providing the requisite optical power, IOLs do not provide the accommodation (i.e., the ability to focus on objects at varying distances) that can be attained by a natural lens. However, multi-focal IOLs are known that can provide a certain degree of accommodation (also known as pseudo-accommodation). For example, bifocal diffractive IOLs are available that are capable of providing a near and a far focus.

Trifocal ophthalmic lenses are also known for providing a near and a far focus, as well as an intermediate focus. Such conventional trifocal lenses, however, suffer from a number of shortcomings. For example, they provide intermediate vision at the expense of degradation of the far and/or near vision.

Accordingly, there is a need for enhanced multifocal ophthalmic lenses, and particularly, trifocal ophthalmic lenses. There is also a need for such multifocal lenses in the form of intraocular lenses (IOLs) that can be implanted in patients' eyes, e.g., to replace the natural lens.

SUMMARY

The present invention is generally directed to diffractive ophthalmic lenses, such as trifocal intraocular lenses (IOLs), that provide near and far vision, as well as intermediate vision. The ophthalmic lenses of the invention utilize diffractive structures to direct incident light to three focal regions corresponding to near, intermediate and far vision. For example, the ophthalmic lenses include a plurality of diffractive zones with varying areas so as to cause broadening of optical energy profiles at a near and a far focus generated by those zones, thereby creating an intermediate focus. In some cases, a maximum difference between the areas of the diffractive zones can be, e.g., in a range of about 75% to about 200%.

In one aspect of the invention, a trifocal ophthalmic lens is disclosed that includes an optic having at least one optical surface, and a plurality of diffractive zones that are disposed on a portion of that surface about an optical axis of the optic. At least two of those diffractive zones have different areas so as to cause broadening of optical energy profiles at a near and a far foci of the diffractive zones for generating an intermediate focus. By way of example, the diffractive zones can direct at least about 25% of incident light energy, or preferably at least about 28% of the incident light energy, into each of the near and far foci, while directing at least about 10% of the incident light energy to the intermediate focus. The optical surface can also include a reference profile characterized by a base curve for generating a refractive power corresponding to the far focus. The term "diffractive zone," as used herein, refers to an area of the surface that contains one or more diffractive structures that are repeated, either identically or in accordance with a selected apodization, to generate a diffraction pattern disposed on that surface.

In a related aspect, the diffractive zones exhibit increasing areas as a function of increasing distance from the optical axis. For example, the diffractive zones can be formed as annular zones, wherein a square of the radius of a zone is defined by the following relation:

$$r_i^2 = (2i+1)\lambda f + g(i),$$

wherein i denotes a zone number, $r_i^2$ denotes a square radius of that zone, and $f$ denotes an add power of the near focus relative to the far focus, $\lambda$ denotes a design wavelength, and g(i) denotes a non-constant function of i.

By way of example, the function g(i) can be defined as follows:

$$g(i) = (ai^2 + bi)f,$$

wherein
i denotes the zone number,
a and b are two adjustable parameters, and
$f$ denotes the focal length of the near focus. By way of example, a can be in a range of about 0.1 $\lambda$ to about 0.3 $\lambda$, and b can be in a range of about 1.5 $\lambda$ to about 2.5 $\lambda$, where $\lambda$ denotes the design wavelength.

In another aspect, the invention provides a trifocal ophthalmic lens that comprises an optic having a surface characterized by a base reference curve, and a plurality of annular diffractive structures superimposed on a portion of that base curve about an optical axis of the optic. The diffractive structures exhibit varying widths so as to collectively provide near, intermediate and far vision.

In a related aspect, the diffractive structures exhibit increasing widths as a function of increasing distance from the optical axis. By way of example, the widths of the diffractive structures can increase radially outwardly from the optical axis in a linear or non-linear fashion. By way of example, in some embodiments, the widths increase linearly such that a maximum percentage difference in the widths of the structures range from about 75% to about 200%.

In another aspect, a multifocal ophthalmic lens is disclosed that includes an optic having at least one optical surface, and at least two diffractive zones disposed on that surface. One of the diffractive zones has an area greater than an area of the other zone by a factor in a range of about 75% to about 200% such that the zones collectively provide near, intermediate and far vision.

Further understanding of the invention can be achieved by reference to the following detailed description in conjunction with associated drawings, which are described briefly below:

DETAILED DESCRIPTION

The present invention is generally directed to trifocal ophthalmic lenses, such as intraocular lenses, that provide near, intermediate and far vision. The trifocal ophthalmic lenses of the invention advantageously provide enhanced visual performance for the intermediate vision relative to that typically obtained by conventional trifocal lenses while maintaining, and in many cases exceeding, the near and far visual performance of such conventional lenses. In embodiments discussed below, various aspects of trifocal lenses of the invention are described in connection with intraocular lenses. It should, however, be understood that the principles of the invention can be similarly applied to fabrication of other ophthalmic lenses, such as contact lenses.

Figure 1A:
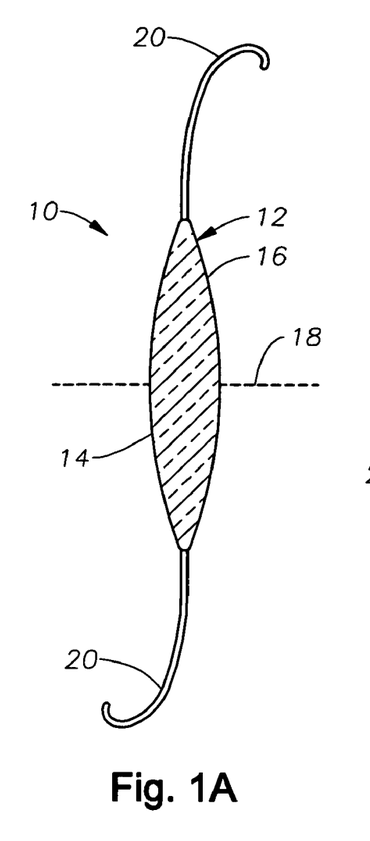
FIG. 1A is a schematic cross-sectional view of a trifocal ophthalmic lens according to one embodiment of the invention.
Figure 1B:
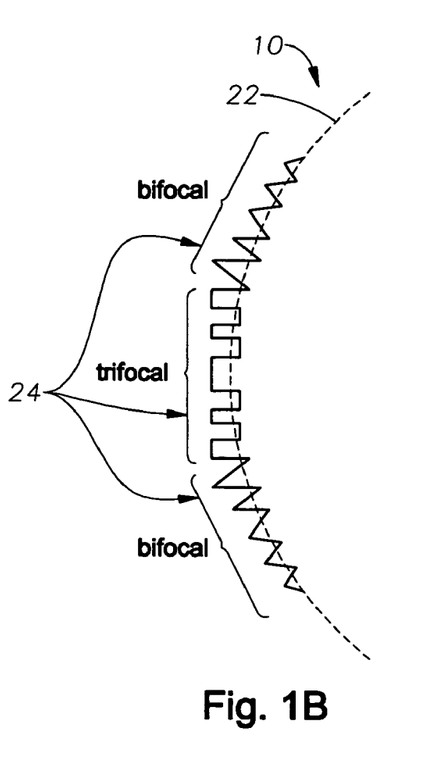
FIG. 1B is a schematic cross-sectional view of an anterior surface of an optic of the lens of FIG. 1A comprising a plurality of diffractive structures superimposed on a base profile.

With reference to FIGS. 1A and 1B, a trifocal ophthalmic lens 10 according to one embodiment of the invention includes an optic 12 having an anterior optical surface 14 and a posterior optical surface 16. In this embodiment, the anterior and the posterior optical surfaces are symmetrically disposed about an optical axis 18 of the lens, although asymmetric surfaces can also be employed. The exemplary lens 10 also includes radially extending fixation members or haptics 20 for its placement in a patient's eye. The optic 12 can be formed of any suitable biocompatible material. Some examples of such materials include, without limitation, soft acrylic, silicone, hydrogel or other biocompatible polymeric materials having a requisite index of refraction for a particular application of the lens. The fixation members 20 can also be formed of suitable polymeric materials, such as polymethylmethacrylate, polypropylene and the like. Although the surfaces 14 and 16 are depicted as being generally convex, either surface can have a generally concave shape. Alternatively, the surfaces 14 and 16 can be selected to provide a plano-convex or a piano-concave lens. The terms "intraocular lens" and its abbreviation "IOL" are used herein interchangeably to describe lenses that are implanted into the interior of an eye to either replace the eye's natural lens or to otherwise augment vision regardless of whether or not the natural lens is removed.

The anterior surface 14 is characterized by a base curve 22 (depicted by dashed lines) that provides a selected refractive power and on which a plurality of diffractive structures 24 are superimposed. As shown schematically in FIG. 2, the diffractive structures 24 can be characterized as forming a plurality of concentric annular diffractive zones 26 that diffract incident light into a plurality of diffractive orders, in a manner discussed in more detail below. The diffractive zones 26 are confined within a portion of the surface that is surrounded by a peripheral portion 28 that is devoid of diffractive structures. In other words, the diffractive zones are truncated such that the peripheral portion of the anterior surface provides a purely refractive power dictated by the base curve. In this embodiment, the diffractive zones are characterized by two diffractive patterns, one of which is herein referred to as a trifocal pattern and the other as a bifocal pattern. More specifically, annular zones 26a, 26b, and 26c, which form the trifocal diffractive pattern, cooperatively direct incident light primarily into three diffraction orders (herein referred to as diffraction orders "+1", "0" and "−1"). The light directed into the diffraction order +1 converges to form a near focus while the light beams directed to diffraction orders 0 and −1 converge to form, respectively, an intermediate and a far (distance) focus. It should be appreciated that the diffractive zones forming the trifocal pattern diffract light into higher orders, as well. However, the trifocal pattern diffracts a large percentage of the incident light, e.g., about 60% or more, into the above three orders.

Figure 2:
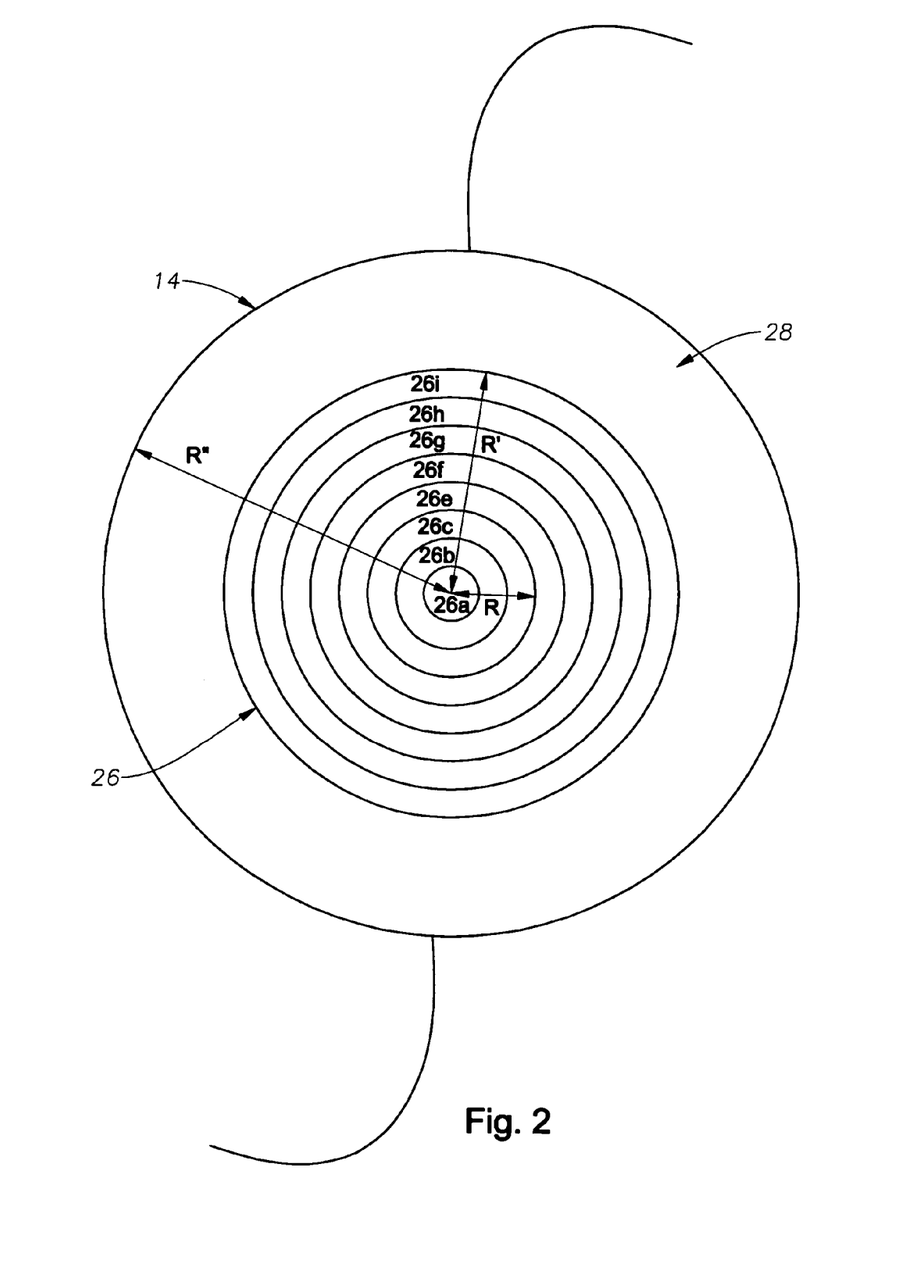
FIG. 2 is a front view of the diffractive lens of the previous figures depicting a plurality of annular zones formed by the diffractive structures.

In this exemplary embodiment, annular diffractive zones 26d, 26e, 26f, 26g, 26h and 26i form the bifocal diffractive pattern, which diffracts the incident light primarily into two diffraction orders (e.g., "0" and "+1" orders). The light diffracted into the $0^{th}$ order of the bifocal pattern converges to a focus that is substantially coincident with the above distance focus generated by convergence of the light diffracted into the −1 order of the trifocal pattern. And the light diffracted into the +1 diffraction order of bifocal pattern converges to a focus that is substantially coincident with the above near focus generated by convergence of the light diffracted into the +1 diffraction order of the trifocal pattern. Similar to the trifocal pattern, the bifocal pattern diffracts light to higher orders, as well. However, it diffracts the bulk of the incident optical energy, e.g., about 60% or more, into the above 0 and −1 orders.

Further, the refractive focus provided by the base curve of the anterior surface substantially corresponds to the far focus generated by the diffractive patterns. That is, the refractive power of the lens contributes to the performance of the lens for far vision As shown schematically in FIG. 1B, in this exemplary embodiment, the trifocal diffractive zones are formed by substantially rectangular diffractive structures (steps), which are separated from one another at their zone boundaries by a substantially uniform step height. By way of example, the step height at a design wavelength can be defined in accordance with the following relation:

$$\text{Step height} = \frac{\lambda}{a(n_2 - n_1)}. \qquad \text{Equation (1)}$$

wherein

λ is the design wavelength (e.g., 550 nm), a denotes a parameter that can be adjusted to control diffraction efficiency associated with various orders. By way of example, a can be selected to be 2.5, $n_2$ is the refractive index of the optic, and $n_1$ denotes the refractive index of the medium surrounding the lens. In embodiments in which the surrounding medium is the aqueous humor having an index of refraction of 1.336, the refractive index of the optic ($n_2$) can be selected to be 1.55. The step height provided by the above equation is only one example, and other step heights can also be utilized.

In contrast, the bifocal diffractive zones in this exemplary embodiment are formed by a plurality of sawtooth-like diffractive structures, which are separated from one another at their respective zone boundaries by non-uniform step heights. More specifically, the step heights at zone boundaries of the bifocal pattern progressively decrease as their distances from the optical axis increase. In other words, the step heights at the boundaries of the bifocal diffractive structures are "apodized" so as to modify the fraction of optical energy diffracted into the near and far foci as a function of aperture size (e.g., as the aperture size increases, more of the light energy is diffracted to the far focus). By way of example, the step height at each zone boundary of the bifocal diffractive pattern can be defined in accordance with the following relation:

$$\text{Step height} = \frac{\lambda}{a(n_2 - n_1)} f_{apodize}. \quad \text{Equation (2)}$$

wherein

λ denotes a design wavelength (e.g., 550 nm), a denotes a parameter that can be adjusted to control diffraction efficiency associated with various orders, e.g., a can be selected to be 2.5, $n_2$ denotes the index of refraction of the optic, $n_1$ denotes the refractive index of a medium in which the lens is placed, and $f_{apodize}$ represents a scaling function whose value decreases as a function of increasing radial distance from the intersection of the optical axis with the anterior surface of the lens. By way of example, the scaling function $f_{apodize}$ can be defined by the following relation:

$$f_{apodize} = 1 - \left(\frac{r_i}{r_{out}}\right)^3. \quad \text{Equation (3)}$$

wherein $r_i$ denotes the radial distance of the $i^{th}$ zone, $r_{out}$ denotes the outer radius of the last bifocal diffractive zone.

Other apodization scaling functions can also be employed, such as those disclosed in a co-pending patent application entitled "Apodized Aspheric Diffractive Lenses," filed Dec. 1, 2004 and having a Ser. No. 11/000770, which is herein incorporated by reference. Further, the diffractive structures can have geometrical shapes different that those described above.

Figure 3:
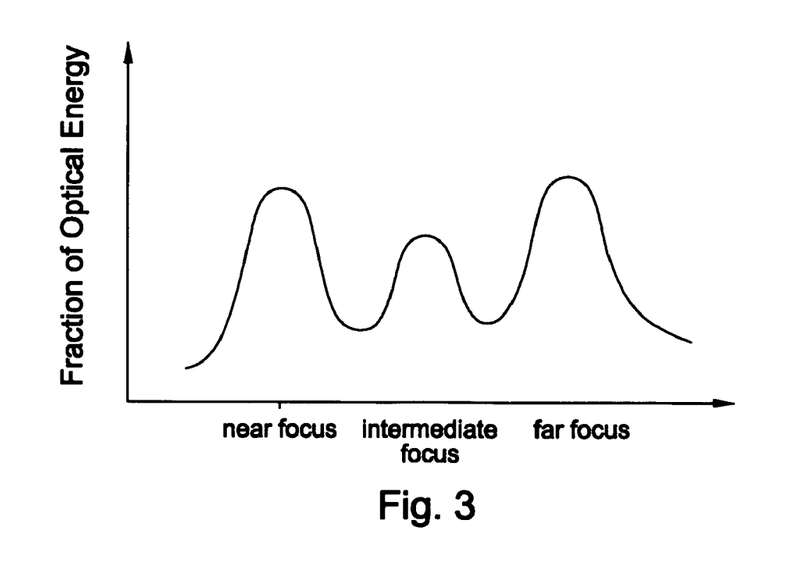
FIG. 3 shows an exemplary distribution of optical power at the near, intermediate and far focal regions of a trifocal ophthalmic lens according to one embodiment of the invention, FIG. 4A schematically depicts focusing of light emanating from a near, an intermediate and a far object onto the retina of an eye in which a trifocal IOL lens according to an embodiment of the invention is implanted.

Although the diffractive properties of the trifocal and bifocal patterns were discussed separately above, the two patterns cooperatively generate the near, intermediate and far foci for providing, respectively, near, intermediate and far vision. As shown schematically in FIG. 3, at each focus, the optical energy is distributed according to a profile that exhibits a maximum at the focal point and decreases at both sides of that point. A width of the diffractive energy profile (e.g., full-width at half maximum) associated with each focal point provides a measure of the associated depth of focus. In some embodiments, the fraction of incident optical energy (e.g., in the form of substantially parallel incident rays) directed to each of the near and far focal regions relative to that directed to the intermediate focal region can be in a range of about 1.4 to about 4. By way of example, the diffractive efficiency associated with each of the near and far foci can be in a range of about 28% to about 38%, while the diffractive efficiency associated with the intermediate focus lies in a range of about 10% to about 28%.

Referring again to FIG. 2, in this embodiment, the trifocal diffractive pattern extends from the optical axis to a distance (radius) R from that axis, while the bifocal diffractive pattern extends from the distance R to a greater radial distance R' (less than a radius R" of the anterior surface). Hence, for small aperture (pupil) sizes, the near, intermediate and far vision properties of the lens are primarily determined by the trifocal diffractive pattern. As the aperture (pupil) size increases, the properties of the lens are primarily dictated by the bifocal diffractive pattern. In this embodiment, as the aperture size increases, the fraction of optical energy directed to the near and far foci relative to that directed to the intermediate focus increases. Moreover, as noted above, the apodization of the step heights of the bifocal diffractive zones results in an increase in the optical energy directed to the far focus relative to the near focus, as the aperture size increases. Generally, the radius of the optic (R") is selected to be in a range of about 2.5 to about 3.5 millimeters, with the radius of the trifocal pattern (R) lying in a range of about 1 to about 1.5 millimeters and that of the bifocal pattern (R') in a range of about 1.5 to about 2 millimeters—although other values can also be employed. Further, although only a few annular zones are depicted herein for clarity, the number of annular zones in each of the trifocal and the bifocal patterns can be generally in a range of about 3 to about 30, and can be more based on increase in the add power.

The optical power associated with the far focus can be, e.g., in a range of about 6 to about 34 Diopters. The intermediate focus can provide an add power in a range of about 1.5 to about 4.5 Diopters, and the near focus can provide an add power in a range of about 3 to about 9 Diopters.

Figure 4A:
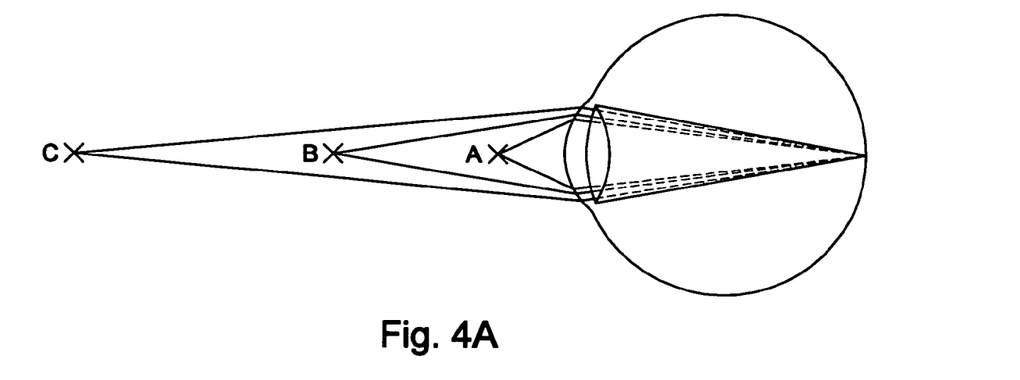

Thus, the above trifocal IOL lens 10 provides far vision for viewing objects at distances ranging, e.g., from about infinity to about 4 meters (m), and near vision for viewing objects, at distances less than, e.g., about 0.4 m. In addition, the IOL 10 provides intermediate vision for viewing objects at distances in a range of, e.g., about 0.4 to about 4 m (and in some embodiments in a range of about 0.4 to about 1 m). In other words, the above trifocal ophthalmic lens advantageously provides a degree of accommodation (typically referred to as pseudoaccommodation) for three distance ranges. By way of further illustration, as shown schematically in FIG. 4A, when the trifocal IOL is implanted in a patient's eye, the combined power of the eye's cornea and the near, intermediate, and far power of the IOL allow focusing light emanating from objects A, B, and C, located, respectively, within a near, an intermediate and a far distance range of the patient onto the retina.

Figure 4B:
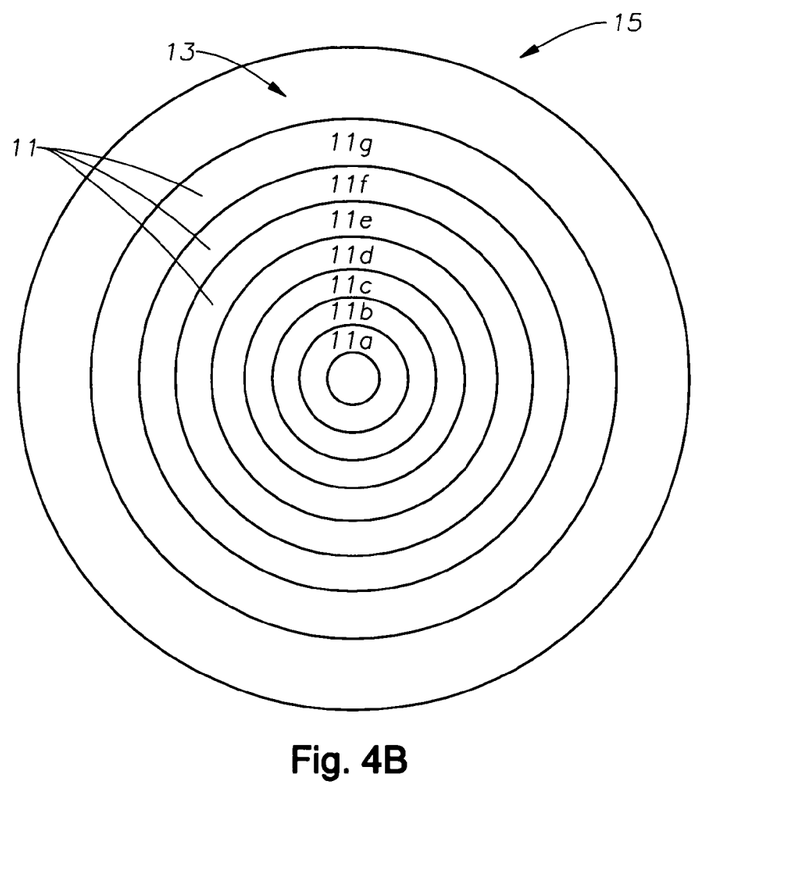
FIG. 4B is a schematic front view of a trifocal ophthalmic lens according to another embodiment of the invention having inner and outer bifocal diffractive patterns with different add powers selected such that the patterns collectively provide near, intermediate and far vision, FIG. 4C schematically depicts optical energy profiles at near and far foci of individual bifocal patterns of the lens shown in FIG. 4B, as well as the energy profiles at near, intermediate and far foci collectively provided by the combined patterns.
Figure 4C:
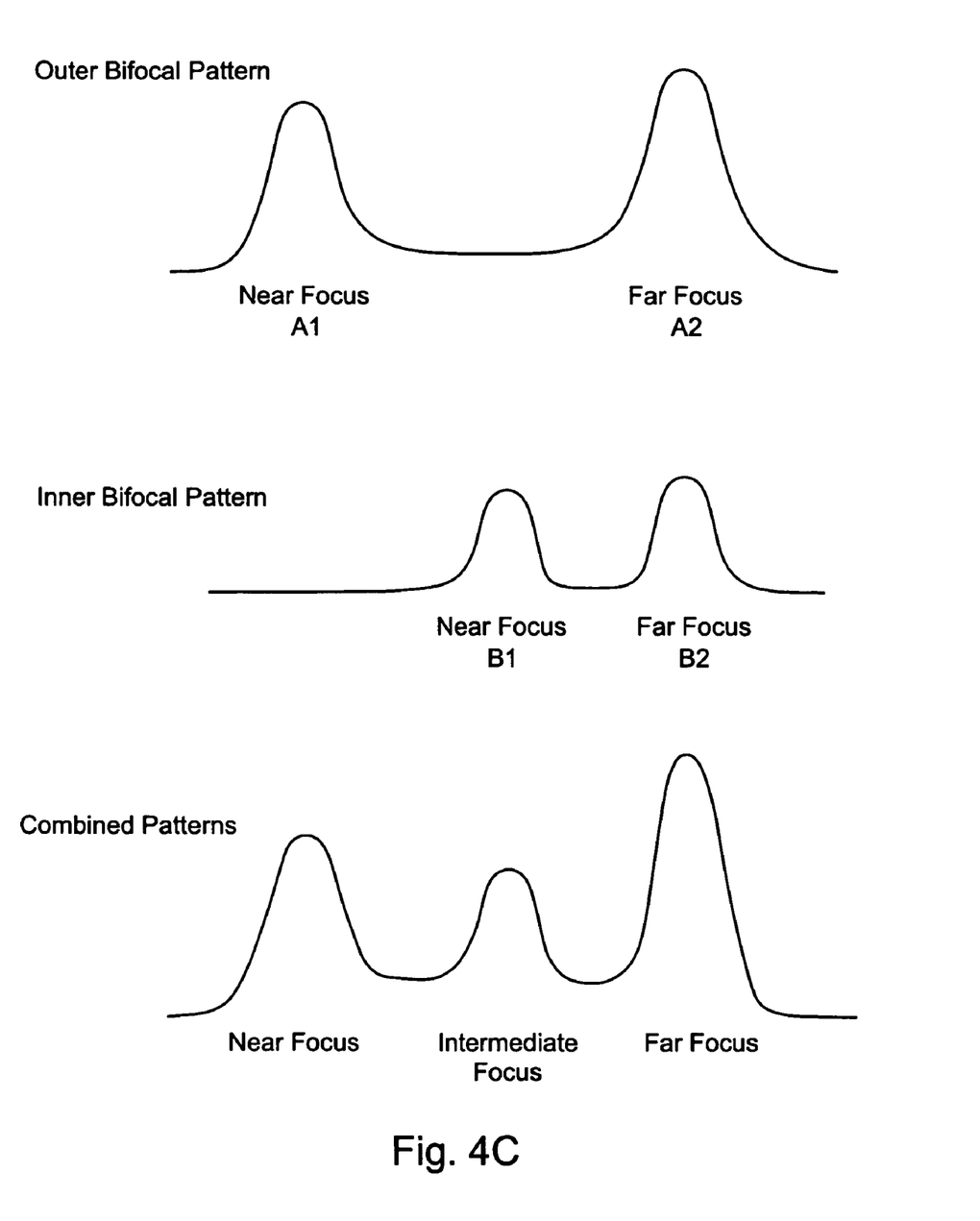

In some embodiments, a trifocal ophthalmic lens of the invention includes two bifocal patterns—providing different add powers—that are disposed on a surface thereof such that they collectively provide three focal regions corresponding to far, intermediate and near vision. By way of example, FIG. 4B schematically illustrates a plurality of diffractive zones 11, formed of two different bifocal patterns, disposed on a portion of an anterior surface 13 of a trifocal lens 15 according to another embodiment of the invention. Similar to the previous embodiment, the anterior surface is characterized by a base profile (not shown) that provides a far focus power corresponding to the $0^{th}$ diffraction order of each pattern. More specifically, the inner diffractive zones 11a, 11b, and 11c form a bifocal pattern providing one selected add power, e.g., an add power in a range of about 3 to about 9 Diopters, while the diffractive zones 11d, 11e, 11f, and 11g form another bifocal pattern that provides a different add power, e.g., an add power in a range of about 1.5 to about 4.5 Diopters (the diffraction zones are shown only for illustration purposes and are not necessarily drawn to scale). Although in this embodiment, the inner bifocal pattern exhibits a higher add power than the outer bifocal pattern, in other embodiments, the outer pattern provides a greater add power. Further, although only a few diffraction zones are illustrated, in many embodiments, the number of diffraction zones in each pattern can range from about 3 to about 30, or any other suitable number. The step heights at zone boundaries can be uniform or non-uniform and can be selected, e.g., in a manner discussed above. The add power of each zone can be set by selecting the locations of its zone boundaries (i.e., the radial distance of each diffractive zone in the pattern) in accordance with the following relation:

$$r_i^2 = (b\,2i+1)\lambda f \qquad \text{Equation (4)}$$

wherein i denotes the zone number (i=0 denotes the central zone), $\lambda$ denotes the design wavelength, and $f$ denotes an add power.

In this exemplary embodiment, the outer bifocal pattern exhibits a greater add power than the inner bifocal pattern. For example, the outer and the inner bifocal patterns can provide, respectively an add power of about 4D and about 2D corresponding to their +1 diffraction orders. The $0^{th}$ diffraction orders of the two patterns are, however, substantially coincident and direct the incident light to a far focal region characterized by a selected power (based on the curvature of the surface of the optic and its index of refraction) in a range of about 6 to about 34 Diopters. As shown schematically in FIG. 5C, the outer pattern provides a far focus A1 and an near focus A2 while the inner pattern provides a far focus B1 (substantially coincident with A1) and a near focus B2. Hence, the two patterns provide collectively a far, an intermediate and a near focus, in which the near focus of the inner and outer patterns provide, respectively, near and intermediate vision.

Figure 5A:
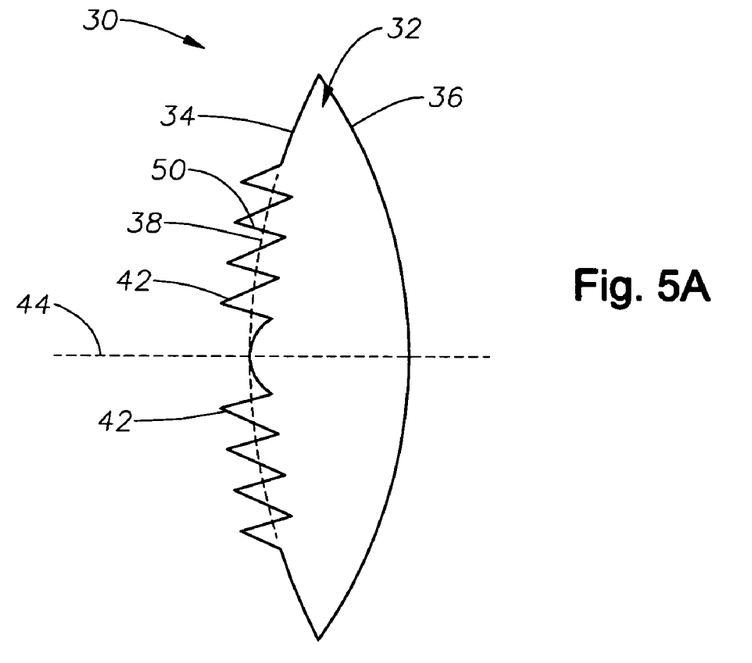
FIG. 5A is a schematic cross-sectional view of a trifocal ophthalmic lens according to another embodiment of the invention having diffractive zones with unequal areas.
Figure 5B:
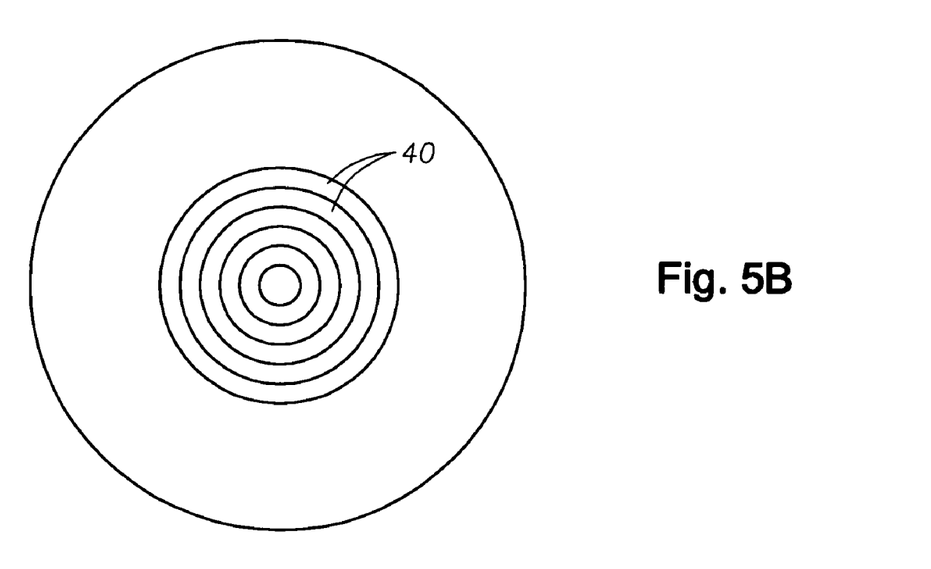
FIG. 5B is a front view of the ophthalmic lens of FIG. 5A.

FIG. 5A and 5B schematically depict a trifocal ophthalmic lens 30, e.g., an IOL, in accordance with another embodiment of the invention that includes an optic 32 having an anterior surface 34 and a posterior surface 36. The reference profile of the anterior surface 34 is characterized by a base curve 38 adapted to provide a far focus power. The anterior surface 34 further includes a plurality of annular diffractive zones 40, formed by a plurality of microscopic diffractive structures 42, that are symmetrically disposed about an optical axis 44 of the optic. Similar to the previous embodiments, the optic can be formed of a biocompatible material, and the lens can further include haptics (not shown) that facilitate its fixation in the eye. Moreover, although the surface 14 and 16 in this embodiment are generally concave, in other embodiments, the surface curvatures can be selected to provide a plano-convex or plane-concave lens.

Each annular diffractive zone is separated from an adjacent zone by a step (e.g., step 50 separating the second zone from the third zone). The steps are positioned at the radial boundaries of the zones. In this embodiment, the step heights are substantially uniform, although in other embodiments they can be apodized, e.g., in a manner discussed above.

Unlike conventional diffractive lenses in which the diffractive zones have substantially uniform areas, in this embodiment, the areas of the diffractive zones vary—in a controlled manner—as a function of distance from the optical axis 44. This variation is designed to sufficiently broaden optical energy profiles at a near and a far focus, generated by two diffraction orders of the diffractive zones, so as to provide an intermediate vision while substantially preserving the near and far foci. For example, referring to FIG. 5B, in this embodiment, the areas of the annular diffractive zones 40 progressively increase as a function of increasing distance from the optical axis. For example, the maximum difference between areas of two diffractive zones (e.g., the difference in the areas of the outer and inner most zones can be about 75% or more, for example, up to about 200%).

Figure 6:
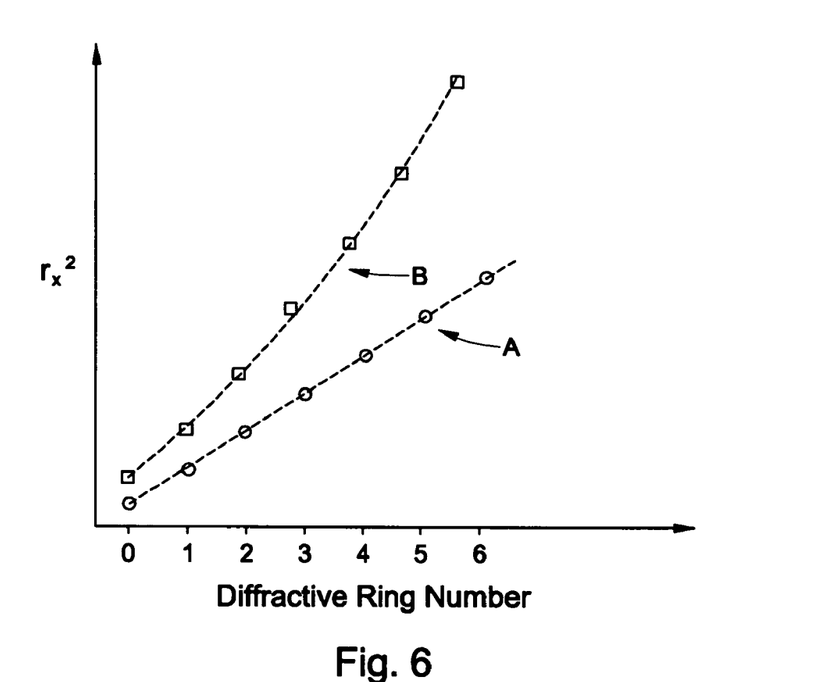
FIG. 6 presents two schematic graphs contrasting relationships between the square radii of the diffractive zones of two diffractive lenses, in one of which the diffractive zones exhibit uniform areas and in the other they exhibit non-uniform areas.

The variation of diffractive zone areas can be implemented by selecting a square radius of each zone as a function of that zone's number, where the zones are consecutively numbered radially outwardly from the optical axis, e.g., in a manner described below. By way of example, FIG. 6 provides graphs contrasting a relationship (Graph A) between the square radii of the zones ($r_i^2$ denotes the square radius of the $i^{th}$ zone) and the zone numbers—typically employed in conventional diffractive lenses—with a different relationship (Graph B) utilized in this embodiment of a trifocal ophthalmic lens of the invention. As noted in the graphs, in the trifocal lens, the square radii of the zones exhibit a selected degree of non-linear variation as a function of the zone numbers while the square radii of the zones of lens having uniform diffractive areas vary linearly as a function of the respective zone numbers. This modifies the interference pattern of light diffracted by the lens so as to divert more energy into an intermediate focal region.

More specifically, in the present embodiment, the radial location of a zone boundary can be determined in accordance with the following relation:

$$r_i^2 = (2i+1)\lambda f + g(i) \qquad \text{Equation (5).}$$

wherein i denotes the zone number (i=0 denotes the central zone), $\lambda$ denotes the design wavelength, $f$ denotes a focal length of the near focus, and g(i) denotes a non-constant function.

In this embodiment, the function g(i) is defined in accordance with the following relation:

$$g(i) = (ai^2 + bi)f,$$

wherein i denotes the zone number, a and b are two adjustable parameters, and $f$ denotes the focal length of the near focus. By way of example, a can be in a range of about $0.1\,\lambda$ to about $0.3\,\lambda$, and b can be in a range of about $1.5\,\lambda$ to about $2.5\,\lambda$, where $\lambda$ denotes the design wavelength.

As noted above, the variation of the areas of the diffractive zones as a function of distance from the optical axis results in diversion of some of the diffracted light into an intermediate focal region for providing intermediate vision. For example, a fraction of the diffracted light in a range of about 10% to about 28% can be directed into the intermediate focal region.

Figure 7:
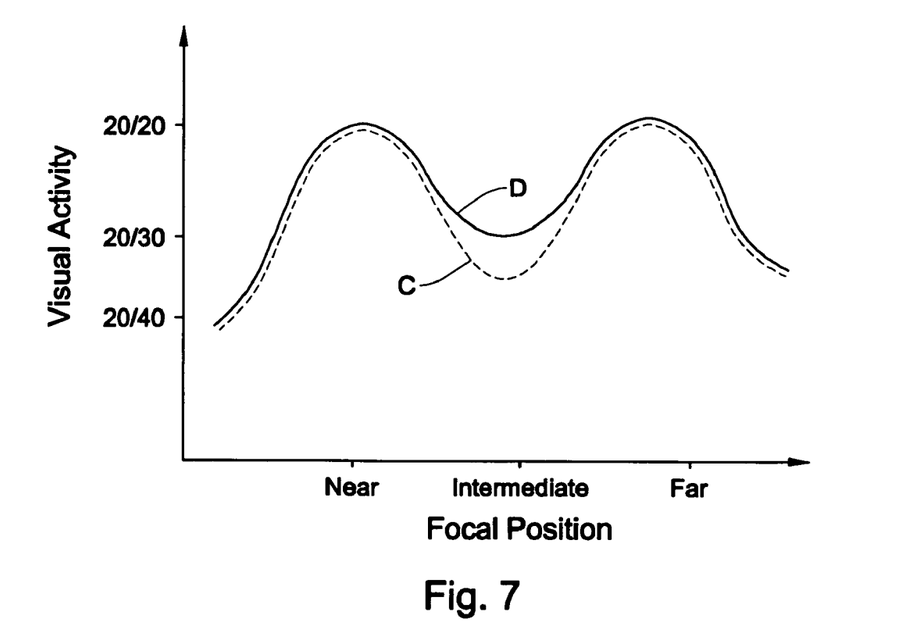
FIG. 7 presents two schematic graphs illustrating the enhancement of visual acuity for intermediate vision provided by a trifocal ophthalmic lens according to one embodiment of the invention, FIG. 8 schematically depicts the optical phase delay (OPD) associated with three diffraction orders of a multifocal diffractive ophthalmic lens across two diffractive orders as a function of the square radial distance from the lens's optical axis.

By way of example, FIG. 7 presents two graphs (C and D) schematically illustrating the enhancement of visual acuity for intermediate vision provided by the above exemplary trifocal ophthalmic lens. More specifically, graph C (dashed lines) shows the distribution of optical energy between a near and a far focus of a conventional diffractive lens in which the annular diffractive zones have equal areas. In contrast, graph D schematically shows the distribution of optical energy in an ophthalmic lens according to an embodiment of the invention in which at least two or more of the diffractive zones have unequal areas. A comparison of graph D with graph C shows that an embodiment of an ophthalmic lens of the invention having diffractive zones with unequal areas provides a considerable enhancement of the visual acuity for intermediate vision, while substantially preserving the visual performance at near and far vision. By way of example, in many embodiments, the diffractive efficiency at each of the near and far foci can be in a range of about 28% to about 38%, with the diffractive efficiency at the intermediate focus lying in a range of about 10% to about 28%.

Similar to the previous embodiment, the optical power associated with the far focus can be, e.g., in a range of about 6 to about 34 Diopters with the near focus providing an add power in a range of about 3 to about 9 Diopters. Further, the intermediate focus can provide, e.g., an add power in a range of about 1.5 to about 4.5 Diopters relative to the far focus.

Figure 8:
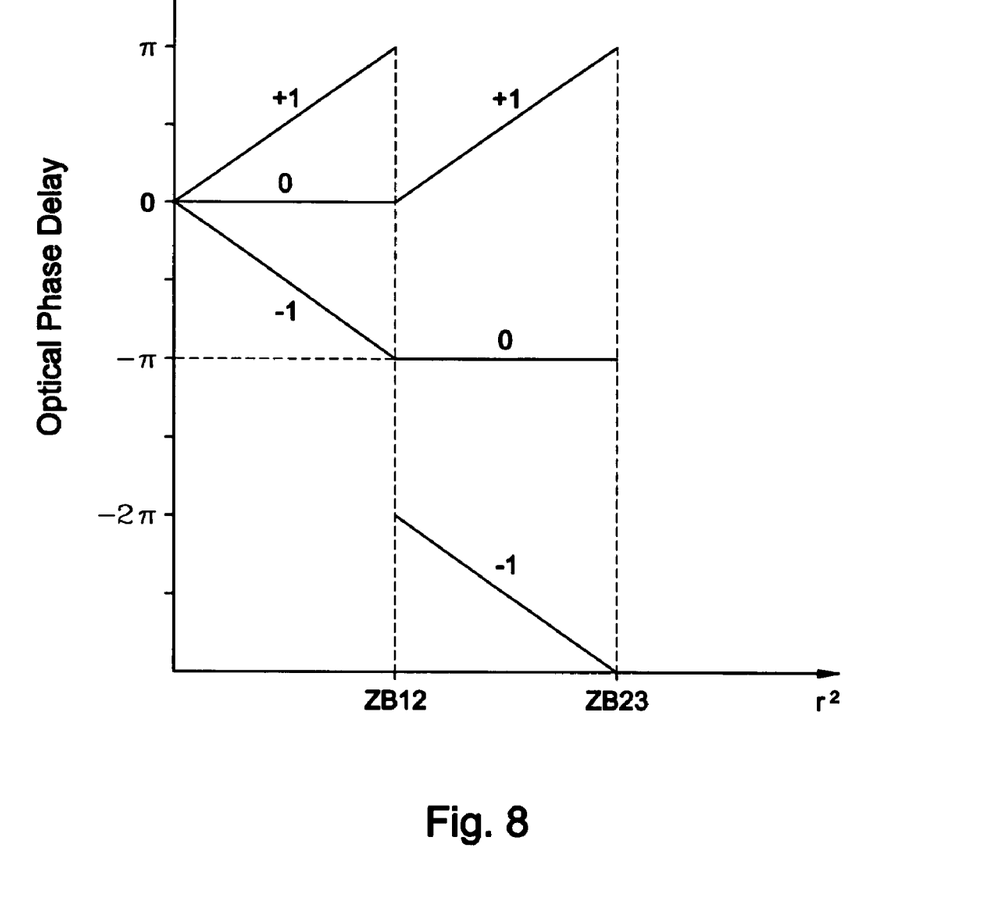

The functionality of the above trifocal lenses can be perhaps better understood by considering the diagram shown in FIG. 8, depicting the optical phase delay (OPD) associated with three diffraction orders (i.e., +1, 0, and −1) of a multifocal diffractive lens across two diffractive zones, as a function of the square of the radial distance from the optical axis. The phase delays associated with the +1 and −1 vary substantially linearly—while that associated with the $0^{th}$ order remains substantially constant—as the square of the radial distance changes from zero to a value corresponding to the boundary of the first diffractive zone with the second (designated herein by ZB12). At the zone boundary, the optical phase associated with each order exhibits a discontinuity. Although not shown, similar phase discontinuity occurs at the boundary of the second zone with the third (designated at ZB23), etc. If the zone boundaries are placed at square radial positions corresponding to $\pi$ optical phase change across each diffractive zone, the optical energy diffracted into the $0^{th}$ order substantially vanishes. In other words, the lens provides effectively only two diffraction orders (near and far focus). However, in many embodiments of the invention, the square radial locations of one or more diffractive zone boundaries are selected such that the optical phase change across a diffractive zone is less than $\pi$ (e.g., it is $\pi/4$). This leads to diversion of some of the diffracted optical energy into the $0^{th}$ order, thereby providing intermediate vision.

In some embodiments, the distance vision provided by the trifocal ophthalmic lens is enhanced by aberration correction for large apertures (e.g., aperture sizes larger than about 3 mm in diameter, though in some embodiments the aberration correction can also be utilized for smaller aperture sizes). Such aberration correction can, for example, counterbalance defocused light, if any, that may appear at the far focus as a result of an increase of light at the intermediate focal region. For example, the base profile (curve) of the anterior surface can be selected to have some degree of asphericity in order to reduce spherical aberration effects, which can be particularly pronounced for large apertures. Some example of such aspherical profiles suitable for use in the practice of the invention are disclosed in the aforementioned copending United States patent application entitled "Apodized aspheric diffractive lenses."

By way of example, the aspherical profile of the anterior surface as a function of radial distance (R) from the lens's optical axis can be characterized by the following relation:

$$z = \frac{cR^2}{1 + \sqrt{1-(1+cc)c^2R^2}} + adR^4 + aeR^6 + \text{higher order terms,}$$

wherein,
z denotes a sag of the surface parallel to an axis (z), e.g., the optical axis, perpendicular to the surface,
c denotes a curvature at the vertex of the surface,
cc denotes a conic coefficient,
R denotes a radial position of the surface,
ad denotes a fourth order deformation coefficient, and
ae denotes a sixth order deformation coefficient.

Those having ordinary skill in the art will appreciate that various modifications can be made to the above embodiments without departing from the scope of the invention.

What is claimed is:

1. A multifocal ophthalmic lens, comprising;
an optic having at least one optical surface; and
a plurality of diffractive zones disposed about an optical axis of the optic, at least two of said diffractive zones having different areas so as to cause broadening of optical energy profiles at a near and a far foci of said diffractive zones for generating an intermediate focus, wherein the diffractive zones comprise annular zones characterized by a radius ($r_i$) from the optical axis, wherein a square of the radius of a zone is defined by the following relation:

$r_i^2 = (2i+1)\lambda f + g(i),$ wherein i denotes a zone number, $r_i^2$ denotes a square radius of that zone, $f$ denotes an add power of the near focus relative to the far focus, $\lambda$ denotes a design wavelength, and g(i) denotes a non-constant function of i.

2. The multifocal lens of claim 1, wherein g(i) is defined by the following relation:

$g(i) = (ai^2 + bi)f,$ wherein
i denotes the zone number,
a and b are two adjustable parameters, and
$f$ denotes the focal length of the near focus.

3. The multifocal lens of claim 2, wherein said adjustable parameter a is in a range of about $0.1\lambda$ to about $0.3\lambda$.

4. The multifocal lens of claim 3, wherein said adjustable parameter b is in a range of about $1.5\lambda$ to about $2.5\lambda$.

* * * * *